(12) United States Patent
Shen et al.

(10) Patent No.: US 7,678,394 B2
(45) Date of Patent: Mar. 16, 2010

(54) ANALYTICAL METHODS FOR IDENTIFYING GINSENG VARIETIES

(76) Inventors: Baihua Shen, 4/F, No. 239, Fuyou Road, Shanghai (CN) 200010; Zhongkai Yan, No. 1745 Gongnongda Road, Changchun (CN) 130021; Heming Niu, Room 203, No. 13, Middle Siyou street, Guangzhou (CN) 510600

( * ) Notice: Subject to any disclaimer, the term of this patent is extended or adjusted under 35 U.S.C. 154(b) by 0 days.

(21) Appl. No.: 12/058,026

(22) Filed: Mar. 28, 2008

(65) Prior Publication Data
US 2008/0175929 A1    Jul. 24, 2008

Related U.S. Application Data

(63) Continuation of application No. PCT/CN2006/002319, filed on Sep. 7, 2006.

(51) Int. Cl.
*A61K 36/25* (2006.01)
(52) U.S. Cl. .................................................... 424/728
(58) Field of Classification Search ........................ None
See application file for complete search history.

(56) References Cited

U.S. PATENT DOCUMENTS

| | | | |
|---|---|---|---|
| 6,039,950 A * | 3/2000 | Khwaja et al. | 424/727 |
| 6,447,814 B1 * | 9/2002 | Lee et al. | 424/725 |
| 6,896,910 B2 * | 5/2005 | Kim et al. | 424/725 |
| 2003/0059837 A1 * | 3/2003 | Levinson et al. | 435/7.1 |
| 2007/0065526 A1 * | 3/2007 | Gow et al. | 424/728 |

OTHER PUBLICATIONS

Liu et al. J. Molecular Structure. 2008. vol. 883-884, pp. 228-235. CAPLUS Abstract enclosed.*

* cited by examiner

*Primary Examiner*—Christopher R. Tate
(74) *Attorney, Agent, or Firm*—Matthias Scholl P.C.; Matthias Scholl

(57) ABSTRACT

An analytical method for identifying woods-grown ginseng and mountain cultivated ginseng comprise: (a) preparing ginseng extracts, (b) acquiring fingerprint regions by GC-MS analysis, (c) selecting at least 8 GC peaks for similarity calculation; (d) calculating similarity coefficients; and (e) comparing similarity coefficients of samples to those of standards.

12 Claims, 12 Drawing Sheets

ANALYTICAL METHODS FOR IDENTIFYING GINSENG VARIETIES

CROSS-REFERENCE TO RELATED APPLICATIONS

This application is a continuation of International Patent Application No. PCT/CN2006/002319 with an international filing date of Sep. 7, 2006, designating the United States, now pending, and further claims priority benefits to Chinese Patent Application No. 200510030084.4, filed on Sep. 28, 2005. The contents of these specifications are incorporated herein by reference.

BACKGROUND OF THE INVENTION

1. Field of the Invention

This invention relates to analytical methods, and particularly to analytical identification methods applicable to identification of woods-grown ginseng and mountain-cultivated ginseng.

2. Description of the Related Art

Radix ginseng is the dried root of a perennial plant Panax ginseng C. A. Meyer (Araliaceae). Panax ginseng C. A. Meyer (oriental ginseng) comes in at least three varieties depending on where and how it is grown: wild ginseng, woods-grown ginseng, and mountain-cultivated ginseng (also known as garden ginseng). All of these varieties derive from the same root source.

Wild ginseng grows without human interference in remote mountains and dense forests under the conditions of natural climate, soil, slope, forest canopy, moisture and associated plants. It is a perennial, rare and endangered plant, listed as the first class of national protection species in the *Chinese Red Book*, 1$^{st}$ Ed. Wild Panax ginseng is not allowed to be collected and traded in China.

Woods-grown ginseng, seeded artificially, grows in undisturbed natural forest for 15-20 years or longer. The cultivation takes advantage of fertile soil, proper temperature, light and water in a broadleaf forest or a mixed forest of broadleafs and conifers, which imitates the natural growth conditions of wild Panax ginseng. Woods-grown ginseng can be induced to have some of the same characteristics of wild Panax ginseng. Because wild Panax ginseng is increasingly scarce, woods-grown ginseng is the next best thing and is universally sought-after for its medicinal properties.

Mountain-cultivated ginseng is planted in a suitable, hilly area after the area has been logged. Mountain-cultivated ginseng is typically picked after 5-6 years of growth.

The length of cultivation and growth conditions determine ginseng characteristics. Wild ginseng is better in terms of its medicinal properties than wood-grown ginseng, which is in turn better than mountain-cultivated ginseng. However, differentiation of ginseng varieties is difficult based on their exterior characteristics or the characteristics of ground ginseng powder.

The exterior characteristics of ginseng root include the rhizome, the main root, the lateral root, rootlets, and annular marks, which may be used to identify a variety of ginseng. Often, however, exterior characteristics don't reflect the internal quality of ginseng accurately and overemphasis of the usefulness of exterior characteristics in the identification process leads to loss of the consumer confidence.

Chemical characterization work on ginseng has begun as early as in 1939 with a large number of reports appearing in the 1960s. The chemical composition of ginseng extracts is very complicated, with about 200 different compounds having been identified. They are divided into several general classes according to their chemical structures:

1) Terpenes: including monoterpenes, such as $\alpha$-pinene, $\beta$-pinene, dihydrocarvone, carvone, etc; sesquiterpenes, such as straight chain sesquiterpenes nerolidol, cis-farnesene, trans-$\beta$-farnesene, etc, single ring sesquiterpenes, such as $\beta$-bisabolene, $\alpha$-elemene, $\beta$-elemene, etc; bicyclic sesquiterpenes, such as $\alpha$-selinene, $\beta$-selinene, $\beta$-caryophyllene, $\beta$-santalol, etc.
2) Aliphatic compounds, including alkanes, alkenes, alkynes, alcohols, ethers, aldehydes, ketones, acids, esters etc.
3) Aromatic compounds, such as ethylbenzene, tert-butylbenzene, 1,2-dimethyl benzene, naphthalene, naphthylamine, etc.; and
4) Heterocyclic compounds, such as 2-pentylfuran, 5-methyl-2-furfural, benzofuran, teramethyl pyrazine, 1,2-dimethyl anthraquinone, etc.

The amount and contents of various compounds in fresh ginseng extracts vary depending on the length of ginseng growth period and cultivation area, which makes it possible to identify different varieties of ginseng by chromatographic analysis.

The concept of chromatographic fingerprint analysis of complex mixtures is known. By comparing chromatographic fingerprints, samples can be identified. Chromatographic fingerprint analysis involves comparing the similarities and differences (relative intensities) of the corresponding peaks of each chromatogram using a quantization process. Chromatographic fingerprint analysis comprises the following steps: (1). Digitization of the fingerprint (peak measurement, e.g. peak area, peak height etc.); and (2) Calculation of fingerprint spectrum similarity.

In the early research on chromatogram fingerprints, the digitization was realized using the peak height or peak area extracted from the main peak of a chromatogram. However, this method used part of the chromatogram characteristics to express the whole fingerprint, discarding certain information and at last reducing the identification sensitivity of chromatogram fingerprint.

Spectra detected by the modern chromatography are stored as a group of binary numbers in the computer. This group of numbers is called a vector, which conveys the holographic information of the entire spectrum. The similarity measured by this kind of vector reflects the similarity of the entire chromatographic fingerprint of the chemical species. Any chemical species can be expressed by a vector. The resemblance between two chemical species can be measured by the similarity between their vectors.

Chromatogram fingerprint similarity can be calculated from one, several, or all peaks in the chromatogram fingerprint. The latter fingerprint similarity is usually used to measure the overall fluctuation of chemical composition in crude drugs.

Spectra obtained by modern chromatography are usually stored as a group of binary numbers, i.e., a vector. A similarity coefficient S between two chromatographic spectra can be calculated by the following formula:

$$S = \frac{\sum_{i=1}^{n}(x_i - \bar{x})(y_i - \bar{y})}{\sqrt{\sum_{i=1}^{n}(x_i - \bar{x})^2}\sqrt{\sum_{i=1}^{n}(y_i - \bar{y})^2}}$$

In this formula, x̄ and ȳ respectively represent the mean values of two groups of chromatographic numbers and $x_i$ and $y_i$ represent the corresponding points of chromatographic numbers. The obtained related coefficient is $S \in [0,1]$. Thereby, a similarity between the two groups of numbers can be determined. The similarity gained by this method can reflect the resemblance of the entire spectra of two samples.

Gas chromatography (GC) uses gas as the mobile phase. It separates components according to their partition ratios in the immobile phase and gas-carrying phase, which has the advantages of high resolution, good selectivity, rapid measurement and wide applicability. Accordingly, GC is particularly useful in determining relative composition of plant extracts and other volatile mixtures.

GC-MS is a technique which combines mass spectroscopy with gas chromatography. This coupling technique records mass spectroscopic data of various compounds of mixture after they have been resolved by GC. This allows for an easier identification of each peak in a chromatographic fingerprint.

SUMMARY OF THE INVENTION

In one embodiment, this invention provides a method for identifying between woods-grown ginseng and mountain-cultivated ginseng, comprising: (a) preparing a ginseng extract of a ginseng sample; (b) obtaining a GC-MS spectrum of the extract; (c) calculating a similarity coefficient based on at least 8 peaks in the GC-MS spectrum with respect to a selected standard; and (d) comparing the similarity coefficient calculated in (c) to pre-calculated standard similarity coefficients.

In a class of this embodiment, the standard similarity coefficients are: for woods-grown ginseng: main root 0.88-0.91 median mode, 0.77-0.88 mean value mode; lateral root 0.78-0.96 median mode, 0.78-0.96 mean value mode; fibrous root 0.81-0.96 median mode, 0.90-0.92 mean value mode; for mountain cultivated ginseng: main root 0.38-0.57 median mode, 0.36-0.54 mean value mode; lateral root 0.24-0.57 median mode, 0.24-0.58 mean value mode; fibrous root 0.25-0.61 median mode, 0.24-0.71 mean value mode.

In another class of this embodiment, the GC-MS spectrum is obtained at a column temperature rising from 100° C. to 170° C. at 1.5° C./min, then from 170° C. to 190° C. at 8.0° C./min and at last from 190° C. to 240° C. at 2.0° C./min.

In another class of this embodiment, the peaks are common to woods-grown ginseng and mountain-cultivated ginseng samples.

DETAILED DESCRIPTION OF THE EMBODIMENTS

Figure 1:
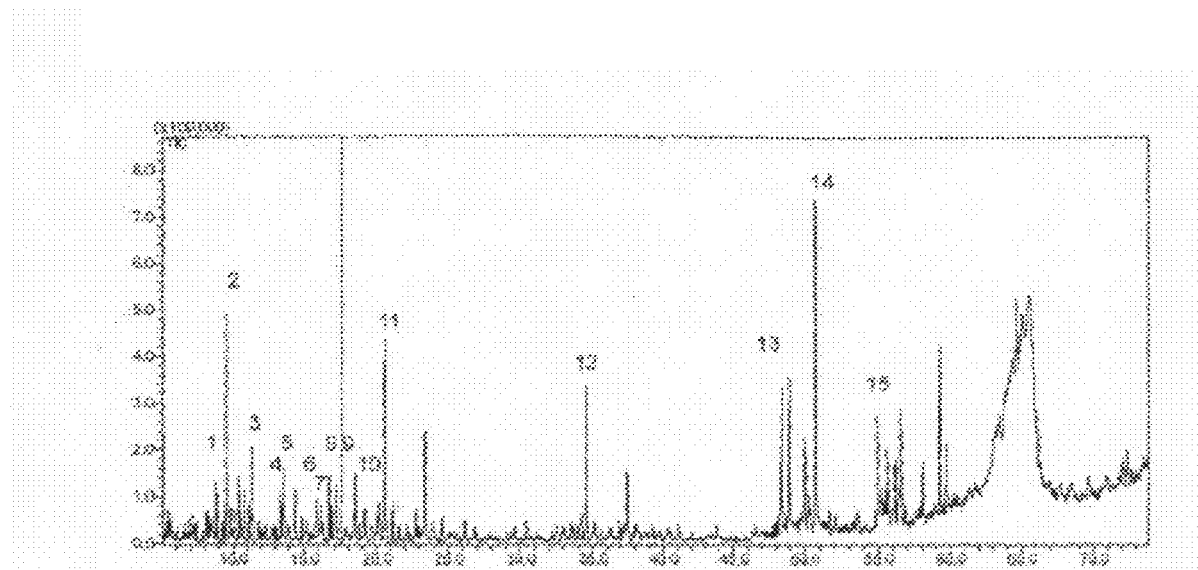
FIG. 1 illustrates a GC-MS chromatogram of ginseng extracts from main root of woods-grown ginseng.

GC-MS technology is used to determine the chemical composition of fresh ginseng extracts via its chromatographic fingerprint. The chromatographic fingerprints of ginseng extracts from various species of ginseng are used to differentiate woods-grown ginseng from mountain-cultivated ginseng. The method of identification according to the invention is based on the following techniques.

1) Preparation of Ginseng Extracts

Various protocols for preparing ginseng extracts were tried to maximize extraction efficiency, wherein the following were varied: extraction solvent (n-hexane, ether, acetone), extraction mode (ultrasound, quench), extraction time (30 min, 1 hr, 2 hrs), extraction temperature (room temperature, 30° C.), and purification (centrifugation, liquid-liquid extraction). The following protocol was determined to be most efficient. Main root, lateral root and rootlets of ginseng were separately broken up into pieces. About 50 mg of each sample was placed into a 1 mL Eppendorf tube, and 0.5 mL of n-hexane were added to each. The samples were sonicated for 1 h and centrifuged. The supernatant was decanted and used directly for GC-MS analysis.

2) Chromatographic Conditions:

Various protocols for GC-MS analysis were tried to maximize resolution, wherein the following were varied: chromatography column, injection volume (1 µL, 3 µL), carrier gas flow rate (1.0, 1.2, 1.3, 1.5 mL/min), and temperature programs (13 various temperature programs). The following protocol resulted in the best resolution: Dikma DM-1 (30 mm×0.25 mm×0.25 um) capillary column; column temperature 100° C.; injection temperature: 270° C.; temperature program (see Table 1); injection volume: 1 µL; injection mode: split stream, split ratio 2.0; flow rate of carrier gas: 1.30 mL/min.

TABLE 1

GC Temperature Program

| Rate (° C./min) | Temperature (° C.) | Hold time (min) |
| --- | --- | --- |
| — | 100.0 | 0.00 |
| 1.5 | 170.0 | 0.00 |
| 8.0 | 190.0 | 0.00 |
| 2.0 | 240.0 | 0.00 |

Experimental Conditions

1) Sample Preparation

Ginseng samples were selected by conventional method. n-Hexane was added and the samples were sonicated for 1 hr. The samples were then centrifuged and the supernatant was decanted for GC-MS analysis.

2) GC-MS Analysis

GC conditions: Dikma DM-1 (30 mm×0.25 mm×0.25 um) capillary column; column temperature: 100° C.; injection temperature: 270° C.; temperature program (Table 1); injection volume: 1 µL; mode of sample injection: split flow, rate of split flow 2.0; flow rate of carrier gas: 1.30 mL/min.

MS conditions: ion source temperature: 200° C.; interface temperature: 250°C.; solvent cut time: 5 min; quality scanning area: m/z 35-380; scanning interval: 0.5 s.

GC-MS charts of the samples were obtained under the conditions listed above.

3) Identification of the Samples

Between 8 and 9 GC peaks were chosen in the chromatographic fingerprint region obtained from step 2) to calculate similarity relative to a standard spectrum (mean or median spectrum of main root, lateral root or rootlets of woods-grown ginsengs).

Then, calculated values were compared with the following standard similarity values to identify the sample as woods-grown ginseng or as mountain-cultivated ginseng.

Woods-Grown Ginseng:
  main root: 0.88-0.91 median mode, 0.77-0.88 typical value mode;
  lateral root: 0.78-0.96 median mode, 0.78-0.96 typical value mode;
  fibrous root: 0.81-0.96 median mode, 0.90-0.92 typical value mode;

Mountain-Cultivated Ginseng:
  main root 0.38-0.57 median mode, 0.36-0.54 typical value mode;
  lateral root 0.24-0.57 median mode, 0.24-0.58 typical value mode;
  fibrous root 0.25-0.61 median mode, 0.24-0.71 typical value mode.

Setting the GC-MS charts of main root, lateral root and rootlets of woods-grown ginseng as the standard of chromatographic fingerprints, by calculating the similarity values between the ginseng sample to be examined and the mutual modes, the identity of a sample (whether woods-grown or mountain-cultivated) can be ascertained.

After extracting 50 µg extracts composition of ginseng using a conventional method, the invention uses examination conditions mentioned above to perform a GC-MS analysis, i.e., to make the GC-MS charts of the extracts as vectors to calculate the similarity value of woods-grown ginseng and cultivated ginseng aided by a computer assessment system of similarity. In this way, woods-grown ginseng can be effectively distinguished from mountain-cultivated ginseng. The method can be also used to determine the part of the ginseng from which extract was made. It can also be used for identification of ginseng powder and other ginseng products.

EXAMPLES

Example 1

Identification Between Woods-Grown Ginseng and Mountain Cultivated Ginseng

1) Equipment and Agent

Shimadzu GC-MS MS-QP2010 gas chromatograph-mass spectrometer

Crest ultrasonic cleaning machine (Model 1875 HTAG)

Spectrafuge 16M Hydroextractor

N-Hexane: Lab-Scan Analytical Sciences, CBAC-34484-2.5 L

2) Sample Source

All the ginseng samples used in the research were purchased from different areas in Jilin Province. See Table 2.

TABLE 2

Type and Geological Origin of Ginseng Samples

| Sample No. | Type | Geological origin |
| --- | --- | --- |
| 1 | Woods-grown ginseng (11-year-old) | Linjiang Region |
| 2 | Woods-grown ginseng (15-year-old) | Linjiang Region |
| 3 | Woods-grown ginseng (18-year-old) | Linjiang Region |
| 4 | Woods-grown ginseng (11-year-old) | Linjiang Region |

TABLE 2-continued

Type and Geological Origin of Ginseng Samples

| Sample No. | Type | Geological origin |
|---|---|---|
| 5 | Woods-grown ginseng (15-year-old) | Linjiang Region |
| 6 | Woods-grown ginseng (18-year-old) | Linjiang Region |
| 7 | Mountain cultivated ginseng (6-year-old) | Jian City |
| 8 | Mountain cultivated ginseng (5-year-old) | Jian City |
| 9 | Mountain cultivated ginseng (4-year-old) | Jian City |
| 10 | Mountain cultivated ginseng (5-year-old) | Jingyu County |
| 11 | Mountain cultivated ginseng (6-year-old) | Jingyu County |

3) Preparation of Sample Extract

Ginseng samples, including main root, lateral root and rootlet samples, were crushed and grinded individually. 50 mg of powder was picked from each sample and sonicated in about 0.5 mL of n-hexane in a 1 mL Eppendorf tube for 60 min. The final solution was centrifuged to obtain clear supernatant liquid for GC-MS analysis.

4) Experimental Condition:

4.1) GC condition: Dikma DM-1 (30 mm*0.25 mm*0.25 μm) capillary column; column temperature: 100° C.; injection temperature: 270° C.; temperature program (Table 1); injection volume: 1 μL; injection mode: split stream, split ratio 2.0; flow rate of carrier gas: 1.30 mL/min.

4.2) MS condition: Ion source temperature: 200° C.; interface temperature: 250° C.; solvent cut time: 5 min; quality scanning area: m/z 35-380; scanning interval: 0.5 s.

5) Chromatogram

FIG. 1 is a GC-MS chromatogram of extracts from the main root of woods-grown ginseng under the experimental conditions mentioned above.

Table 3 shows the characteristic chemical components (characteristic GC peaks) of extracts from the main root of woods-grown ginseng.

TABLE 3

Essential Components of Extracts from Main Root of Woods-grown Ginseng

| Peak No | Name |
|---|---|
| 1 | 5-Methyltetradecane |
| 2 | 5-Isobutylnonane |
| 3 | 5-Butylnonane |
| 4 | β-panasinsene |
| 5 | p-Acetylacetophenone |
| 6 | Paeonal |
| 7 | [1aR-(1aα,7α,7aα,7bα)]-1a,2,3,5,6,7,7a,7b-Octahydro-1,1,7,7a-tetramethyl-1H-cyclopropa[a] naphthalene |
| 8 | α-Caryophyllene |
| 9 | [1aR-(1aα.,4aα,7α,7aβ,7bα)]-Decahydro-1,1,7-trimethyl-4-methylene-1H-Cycloprop[e]azulene |
| 10 | Isocaryphyilene |
| 11 | 8-Methylheptadecane |
| 12 | n-Elcosane |
| 13 | Crocetane |
| 14 | Falcarinol |
| 15 | cis,cis-Linoleic acid |

Figure 2:
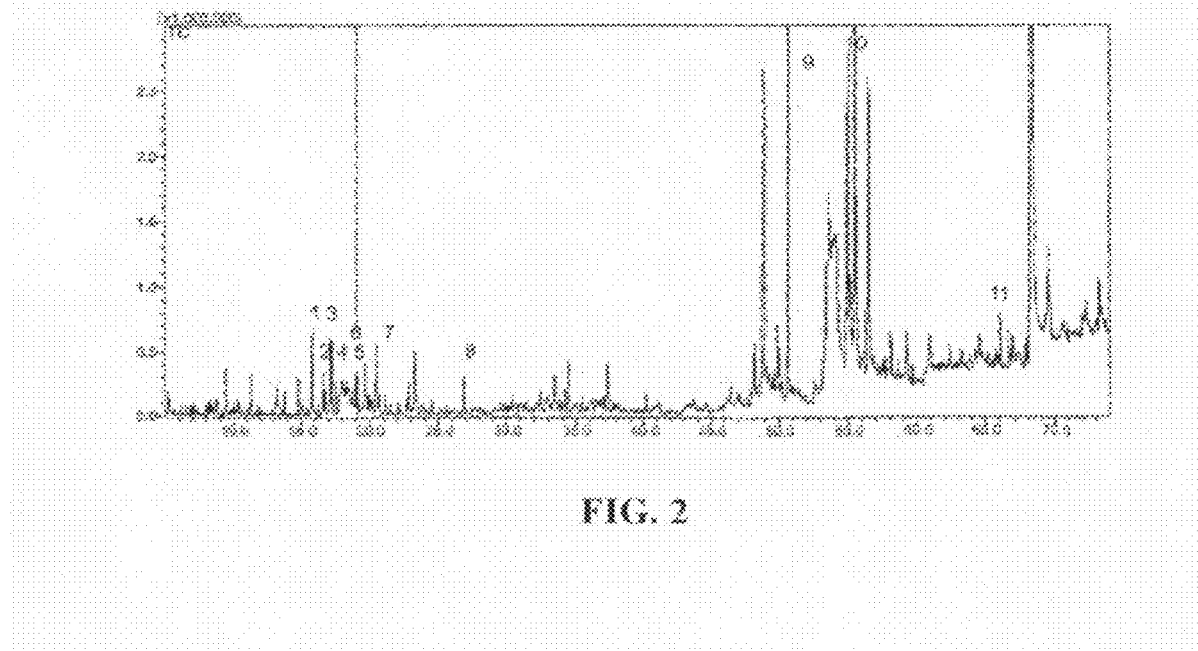
FIG. 2 illustrates a GC-MS chromatogram of ginseng extracts from main root of mountain-cultivated ginseng.
Figure 3:
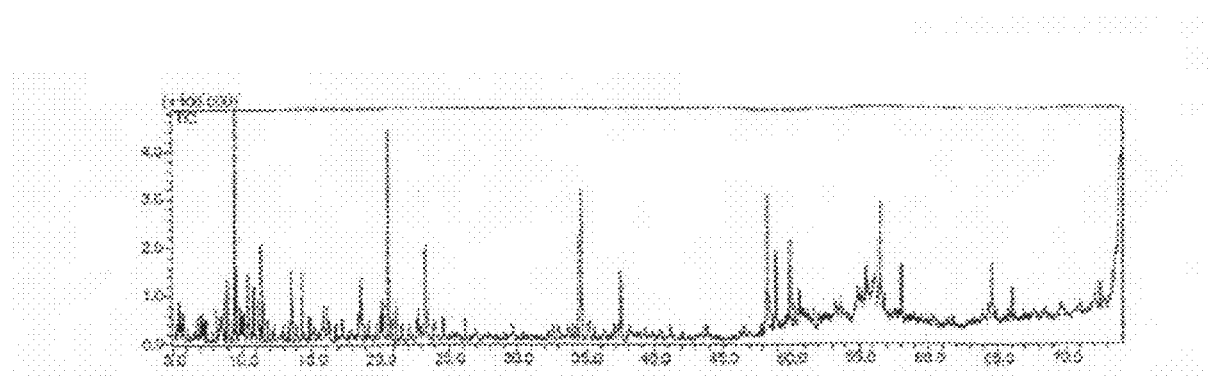
FIG. 3 illustrates a GC-MS chromatogram of ginseng extracts from main root of 15-year-old woods-grown ginseng.
Figure 4:
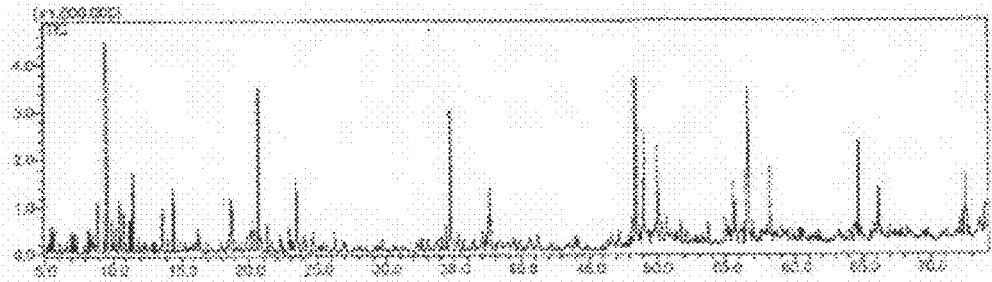
FIG. 4 illustrates a GC-MS chromatogram of ginseng extracts from lateral root of 15-year-old woods-grown ginseng.
Figure 5:
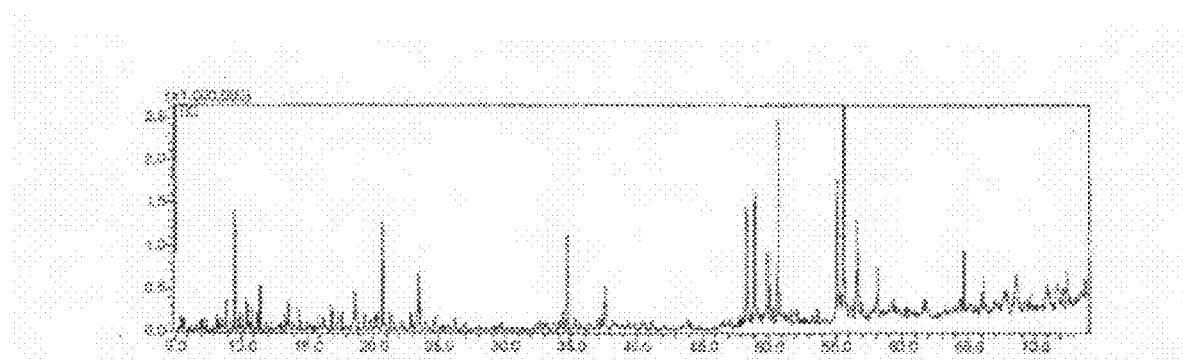
FIG. 5 illustrates a GC-MS chromatogram of ginseng extracts from rootlets of 15-year-old woods-grown ginseng.
Figure 6:
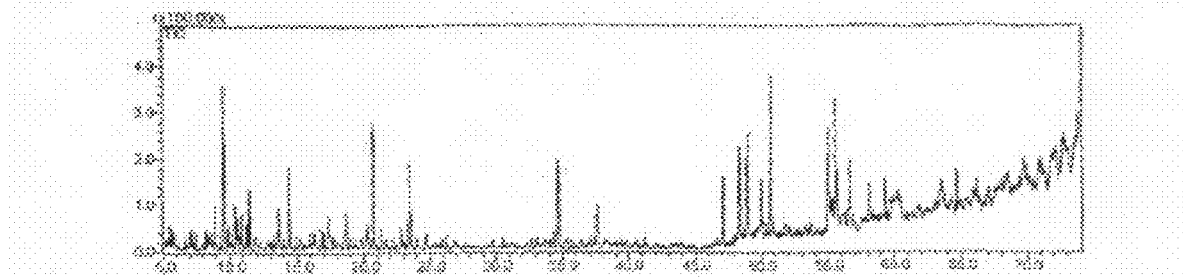
FIG. 6 illustrates a GC-MS chromatogram of ginseng extracts from main root of 18-year-old woods-grown ginseng.

FIG. 2 is a GC-MS chromatogram of extracts from the main root of mountain cultivated ginseng.

Table 4 shows the characteristic chemical components (characteristic GC peaks) of extracts from the main root of mountain cultivated ginseng.

TABLE 4

Essential Components of Extracts from the Main Root of Mountain-Cultivated Ginseng

| Peak No | Name |
|---|---|
| 1 | [1aR-(1aα,7α,7aα,7bα)]-1a,2,3,5,6,7,7a,7b-Octahydro-1,1,7,7a-tetramethyl-1H-cyclopropa[a]naphthalene |
| 2 | Neoclovene |
| 3 | Decahydro-1,1,7-trimethyl-4-methylene-1H-cyclopropa[a]naphthalene |
| 4 | Isobutylnonane |
| 5 | Germacrene B |
| 6 | 2,5-bis(1,1-dimethylethyl)-phenol |
| 7 | 8-Methylheptadecane |
| 8 | n-Heptadecane |
| 9 | Falcarinolol |
| 10 | cis,cis-Linoleic acid |
| 11 | Tetratriacontane |
| 12 | n-Elcosane |

As shown in the figures, the chemical composition of the extracts of ginseng is very complicated, especially at high and low boiling points. The content of polyacetylene-alcohol (having a retention time of around 50 min) appears the highest.

5 batches of woods-grown ginseng were examined and the same number of batches of mountain-cultivated ginseng under the above-mentioned experimental conditions. FIGS. 3, 4, 5 and 6 show GC-MS chromatograms of 3 batches of woods-grown ginseng and 2 batches of mountain cultivated ginseng The above results manifest that extracts from different parts of the same ginseng vary considerably in quantity and content of characteristic chemical components. The differences are even greater than those between different varieties of ginsengs of the same part. The extracts from the same parts of similar samples are roughly the same in composition, proving the comparability between the extracts contents in the same part of the same variety. The comparison between the same parts in woods-grown ginseng and mountain cultivated ginseng can exclude the confounding factors of different parts, thus highlighting the difference of the samples per se.

A standard GC-MS fingerprint of the main root, the lateral root and rootlets from the woods-grown ginseng was established by analysis of the GC-MS chromatograms of the main root, lateral root and rootlets from 3 batches of woods-grown ginseng, which was obtained using the above described protocols as a mean and median. With the standard on hand, the resemblance was calculated between the 2 batches of woods-grown ginseng and 5 batches of mountain cultivated ginseng and the standard. The results were as follows:

1) The standard GC-MS fingerprint and similarity calculation of the extracts from main root of woods-grown ginseng.

1.1) Establishment of the standard of main root in woods-grown ginseng

Samples: sample 4, 5 and 6, or the woods-grown ginsengs of 11, 15 and 18 years old.

Figure 7:
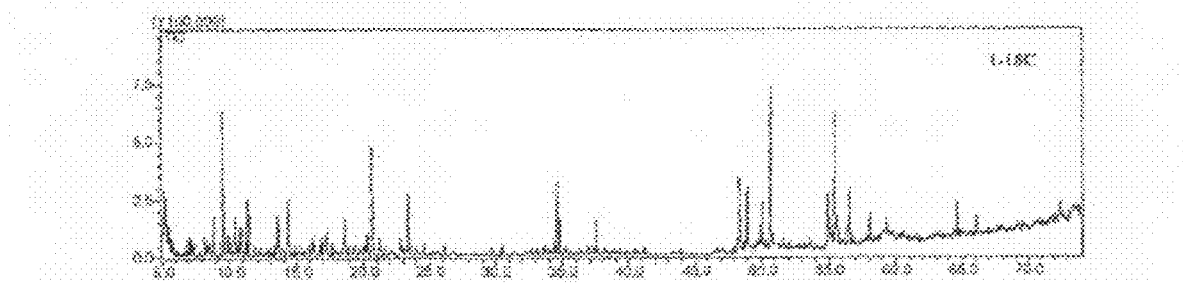
FIG. 7 illustrates a GC-MS chromatogram of ginseng extracts from lateral root of 18-year-old woods-grown ginseng.

Preprocess of data: In the GC-MS chromatograms of three batches of woods-grown ginseng, 8 peaks were selected (marked numerically in FIG. 7). The principle for selecting the peak was as follows:

1.1.1) The main peaks with a high response value were selected in that they were easy to identify and rectify.

1.1.2) The peaks selected appeared in each chromatogram, which enabled every peak to be used in comparisons.

Figure 8:
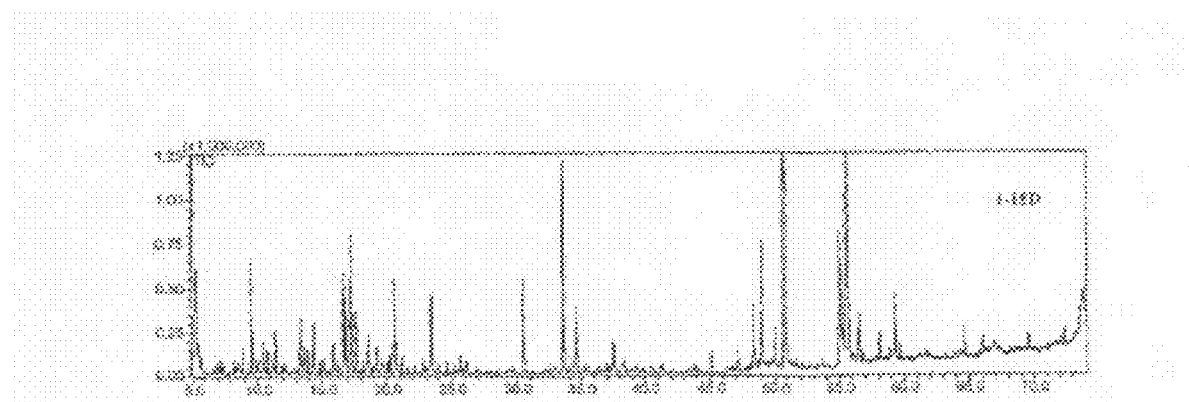
FIG. 8 illustrates a GC-MS chromatogram of ginseng extracts from rootlets of 18-year-old woods-grown ginseng.
Figure 9:
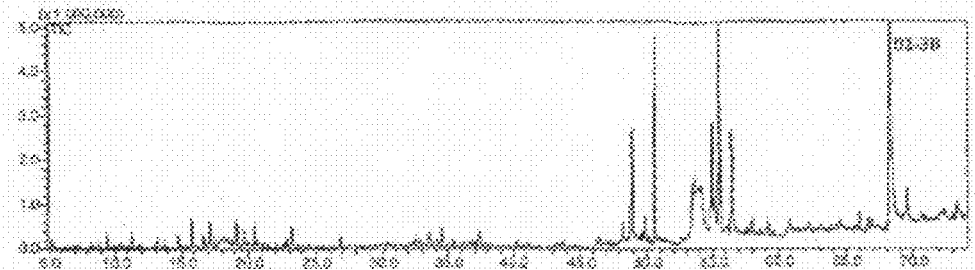
FIG. 9 illustrates a GC-MS chromatogram of ginseng extracts from main root of 4-year-old Jian City mountain-cultivated ginseng.

1.1.3) The chromatographic peaks selected were distributed evenly in the chromatogram and the least square software method was employed in calculations, which made the adjacent chromatographic peak shift simultaneously. The selection ensured that all of the selected chromatographic peaks were used in calculations. FIG. 8 is a chromatogram rectified by means of time calibration via the software of fingerprints of the sample, and FIG. 9 is the standard.

TABLE 5

Similarity in Groups of Main Roots of Three Batches of Woods-grown Ginseng

| No | Sample No | Related Coefficient (median value) | Related Coefficient (mean value) |
|---|---|---|---|
| 1 | 4 | 0.9405 | 0.9359 |
| 2 | 5 | 0.9730 | 0.9353 |
| 3 | 6 | 0.8768 | 0.9441 |

1.2) Similarity Calculation

Figure 10:
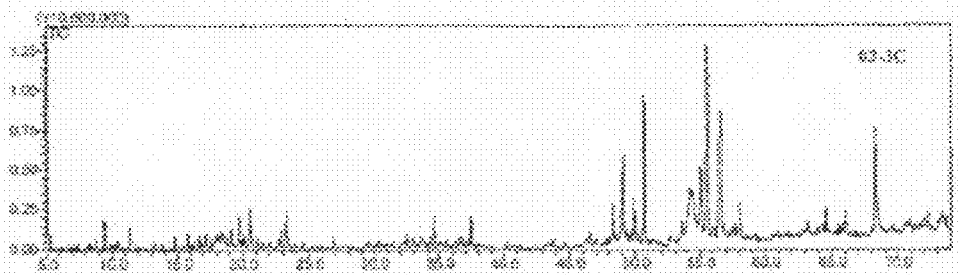
FIG. 10 illustrates a GC-MS chromatogram of ginseng extracts from lateral root of another specimen of 4-year-old Jian City mountain-cultivated ginseng.

With the three woods-grown ginseng fingerprints established by the above method as standards, the similarity between the 3 batches of woods-grown ginseng, and 5 batches of mountain cultivated ginseng (see the GC-MS chromatograms in FIG. 10) and the standards were calculated. (See results in Table 6).

TABLE 6

Similarity between Different Samples of Mountain cultivated Ginseng and Standard of Main Roots of Woods-grown Ginseng

| Chromatogram No. | Sample No. | Sample | Related Coefficient (median value) | Related Coefficient (mean value) |
|---|---|---|---|---|
| 4 | 1 | woods-grown ginseng (11-year-old) | 0.9090 | 0.7925 |
| 5 | 2 | woods-grown ginseng (15-year-old) | 0.8812 | 0.7730 |
| 6 | 3 | woods-grown ginseng (18-year-old) | 0.9071 | 0.8707 |
| 7 | 7 | mountain cultivated ginseng (6-year-old) | 0.4237 | 0.3873 |
| 8 | 8 | mountain cultivated ginseng (5-year-old) | 0.4482 | 0.4228 |
| 9 | 9 | mountain cultivated ginseng (4-year-old) | 0.4495 | 0.3993 |
| 10 | 10 | mountain cultivated ginseng (5-year-old) | 0.3866 | 0.3651 |
| 11 | 11 | mountain cultivated ginseng (6-year-old) | 0.5712 | 0.5431 |

2. The standard GC-MS fingerprint and similarity calculation of extracts from lateral root of woods-grown ginseng.

2.1) Establishment of the standard of lateral root in woods-grown ginseng

Sample: samples 4, 5 and 6, or the woods-grown ginsengs of 11, 15 and 18 years old.

Figure 11:
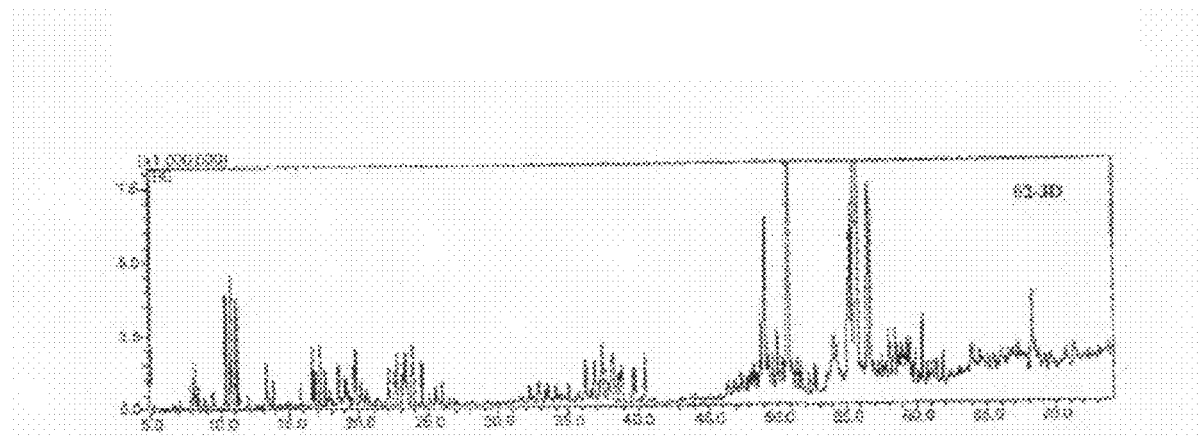
FIG. 11 illustrates a GC-MS chromatogram of ginseng extracts from rootlets of 4-year-old Jian City mountain-cultivated ginseng.
Figure 12:
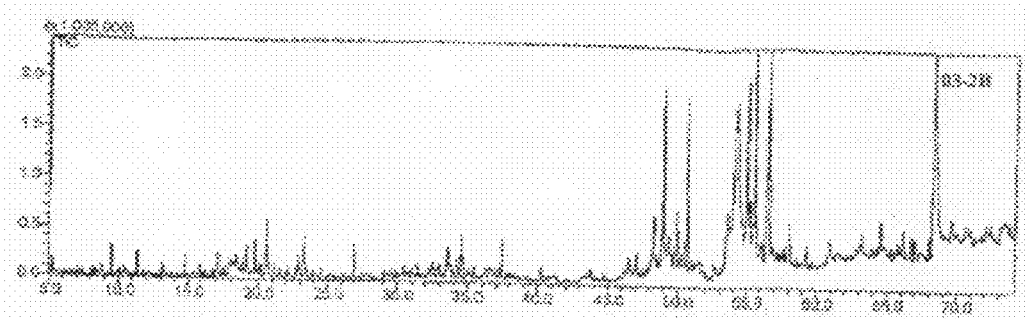
FIG. 12 illustrates a GC-MS chromatogram of ginseng extracts from main root of 6-year-old Jingyu County mountain-cultivated ginseng.

Preprocess of data: In the GC-MS chromatograms of three batches of woods-grown ginseng, 8 peaks were selected (marked numerically in FIG. 11 to be used in calculations. See the rectified chromatogram in FIG. 11; see the standard in FIG. 12 and the similarity between the 3 batches of woods-grown ginseng in Table 7.

TABLE 7

Similarity in Groups of Lateral Roots of Three Batches of Woods-grown Ginseng

| No | Sample No | Related Coefficient (median value) | Related Coefficient (mean value) |
|---|---|---|---|
| 1 | 4 | 0.8973 | 0.9515 |
| 2 | 5 | 0.9002 | 0.9223 |
| 3 | 6 | 0.9511 | 0.9520 |

2.2) Similarity Calculation

Figure 13:
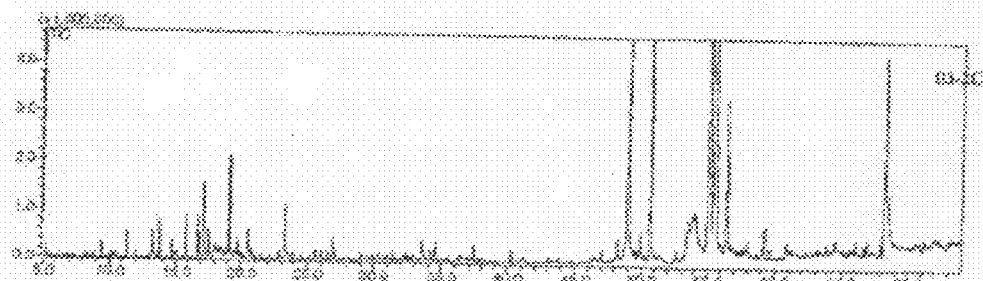
FIG. 13 illustrates a GC-MS chromatogram of ginseng extracts from lateral root of 6-year-old Jingyu County mountain-cultivated ginseng.

With the chosen standard of woods-grown ginseng established by the above method as criterion, the similarity of the GC-MS chromatograms of 2 batches of woods-grown ginseng and 5 batches of mountain cultivated ginseng was calculated (FIG. 13). The result is as follows (Table 8):

TABLE 8

Similarity between Different Samples of Mountain cultivated Ginseng and Standard of Lateral Roots of Woods-grown Ginseng

| Chromatogram No. | Sample No. | Sample | Related Coefficient (median value) | Related Coefficient (mean value) |
|---|---|---|---|---|
| 1 | 2 | Woods-grown ginseng (15-year-old) | 0.7863 | 0.7854 |
| 2 | 3 | Woods-grown ginseng (18-year-old) | 0.9510 | 0.9555 |
| 3 | 7 | Mountain-cultivated ginseng (6-year-old) | 0.5739 | 0.5349 |
| 4 | 8 | Mountain-cultivated ginseng (5-year-old) | 0.5719 | 0.5202 |
| 5 | 9 | Mountain-cultivated ginseng (4-year-old) | 0.5537 | 0.5842 |
| 6 | 10 | Mountain-cultivated ginseng (5-year-old) | 0.2449 | 0.2441 |
| 7 | 11 | Mountain-cultivated ginseng (6-year-old) | 0.4441 | 0.4846 |

3. The common GC-MS mode and similarity calculation of extracts from rootlets of woods-grown ginseng.

3.1) Establishment of the standard of rootlets of woods-grown ginseng

Sample: woods-grown ginseng of 11, 15 and 18 years old.

Figure 14:
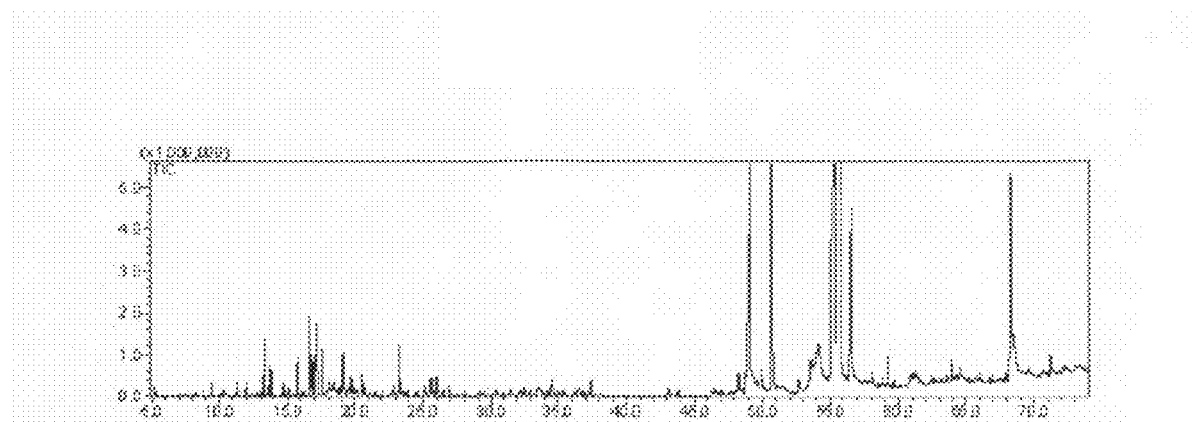
FIG. 14 illustrates a GC-MS chromatogram of ginseng extracts from rootlets of 6-year-old Jingyu County mountain-cultivated ginseng.
Figure 15:
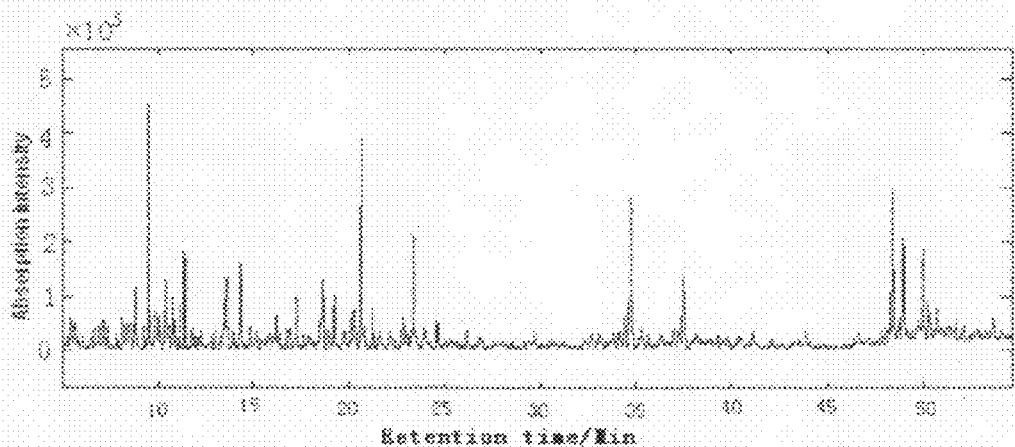
FIG. 15 illustrates a GC-MS calibration spectrogram of ginseng extracts from main roots of three batches of woods-grown ginseng.

Preprocess of data: In the GC-MS chromatograms of three batches of woods-grown ginseng, 9 peaks were selected (marked numerically in FIG. 14) to be used in calculations. See the rectified chromatograms in FIG. 14, the standard in FIG. 15, and the similarity within groups in Table 9.

TABLE 9

Similarity in Groups of Rootlets of Three Batches of Woods-grown Ginseng

| No | Sample No | Related Coefficient (median value) | Related Coefficient (mean value) |
|---|---|---|---|
| 1 | 1 | 0.9610 | 0.9437 |
| 2 | 2 | 0.8937 | 0.8948 |
| 3 | 3 | 0.8093 | 0.9244 |

3.2) Similarity Calculation

Figure 16:
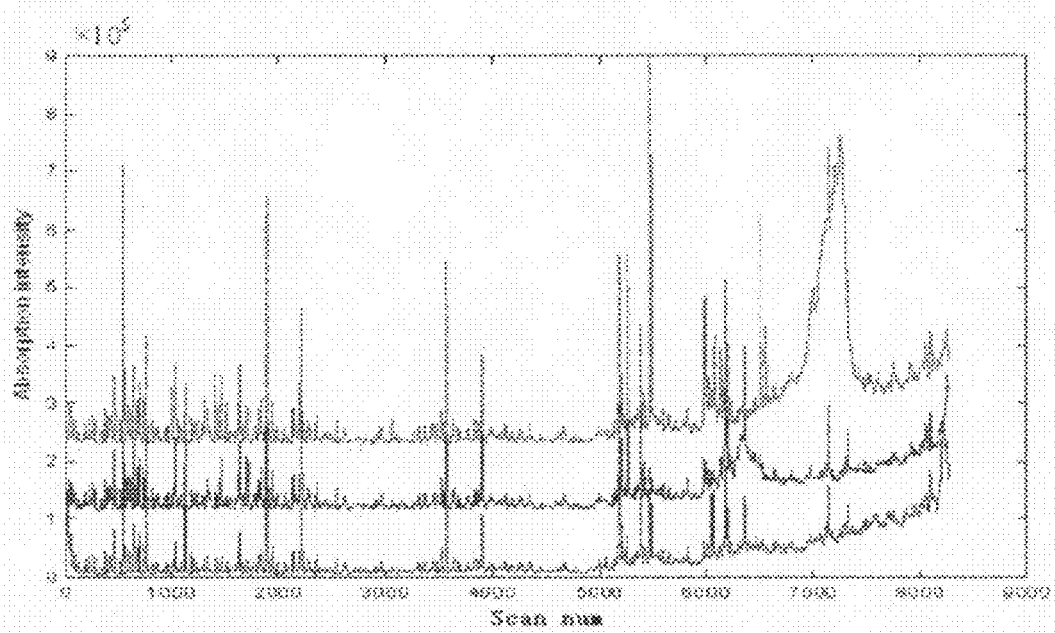
FIG. 16 illustrates a GC-MS chromatogram of ginseng extracts from main roots of three batches of woods-grown ginseng after calibration.
Figure 17:
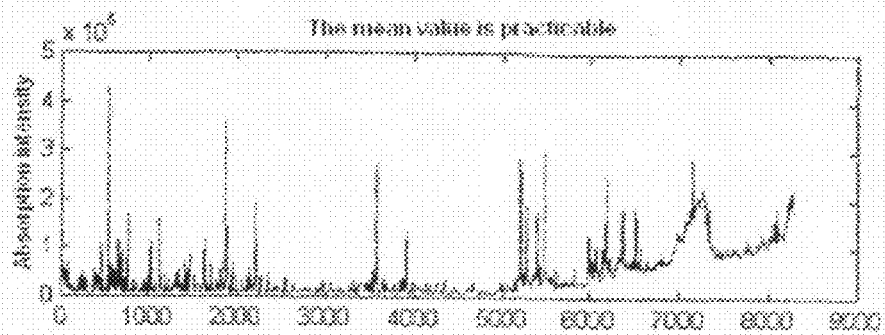
FIG. 17 illustrates a GC-MS chromatogram of a standard of ginseng extracts from main roots of three batches of woods-grown ginseng (mean value)
Figure 18:
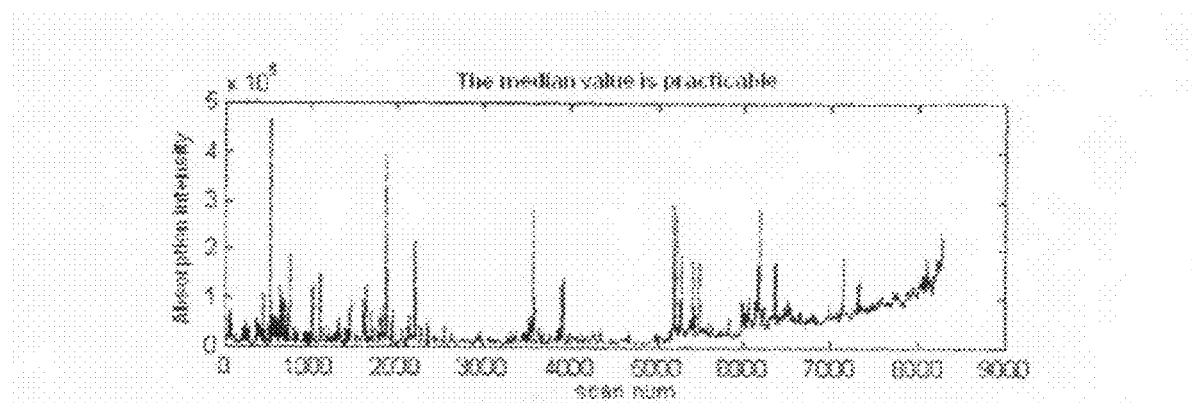
FIG. 18 illustrates a GC-MS chromatogram of a standard of ginseng extracts from main roots of three batches of woods-grown ginseng (median value)
Figure 19:
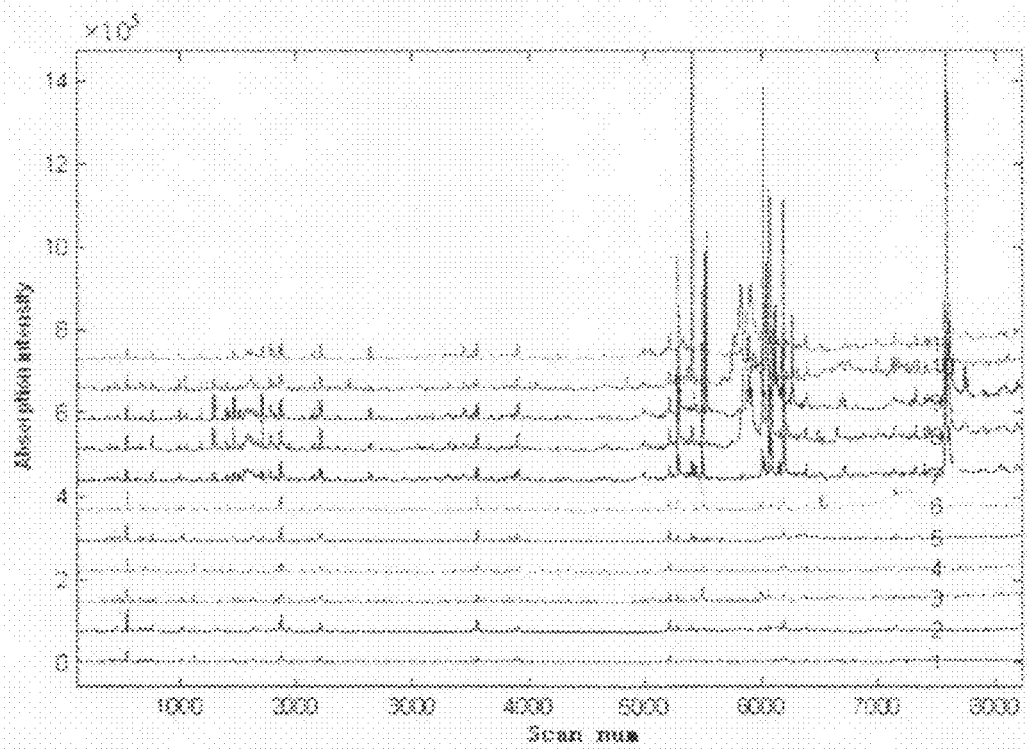
FIG. 19 illustrates a GC-MS chromatogram of ginseng extracts from main roots of three batches of woods-grown ginseng and five batches of mountain-cultivated ginseng after calibration.
Figure 20:
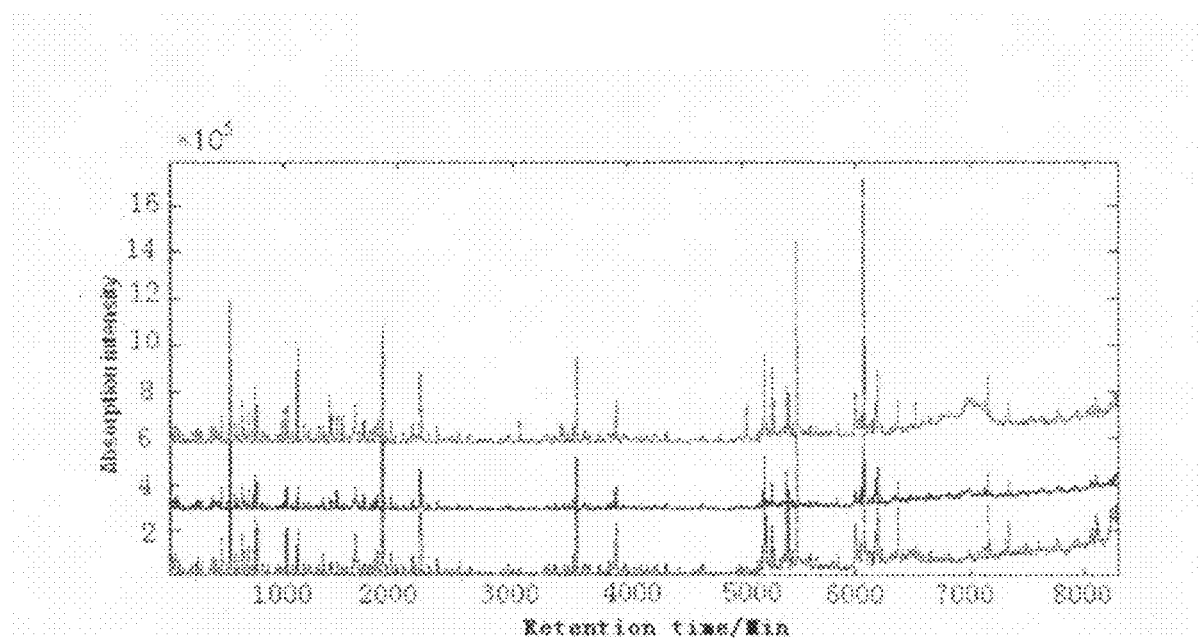
FIG. 20 illustrates a GC-MS chromatogram of ginseng extracts from lateral roots of three batches of woods-grown ginseng after calibration.
Figure 21:
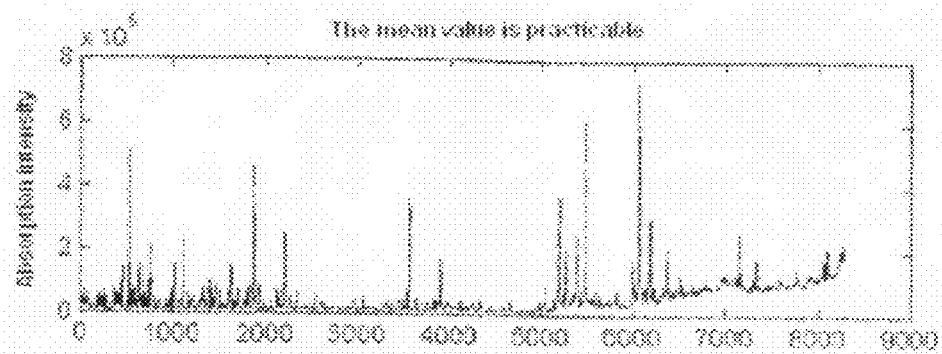
FIG. 21 illustrates a GC-MS chromatogram of a standard of ginseng extracts from lateral roots of three groups of woods-grown ginseng (mean value)
Figure 22:
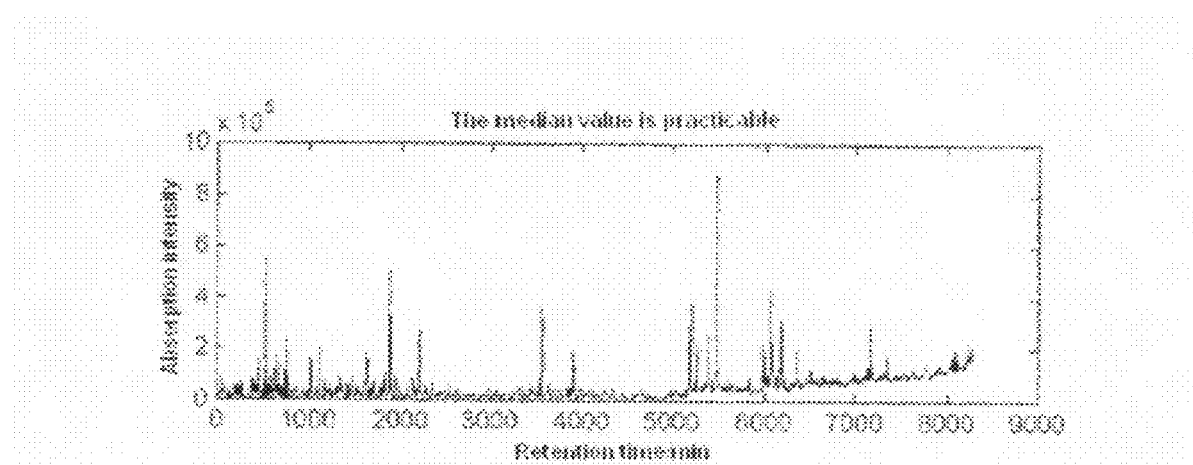
FIG. 22 illustrates a GC-MS chromatogram of a standard of ginseng extracts from lateral roots of three batches of woods-grown ginseng (median value)
Figure 23:
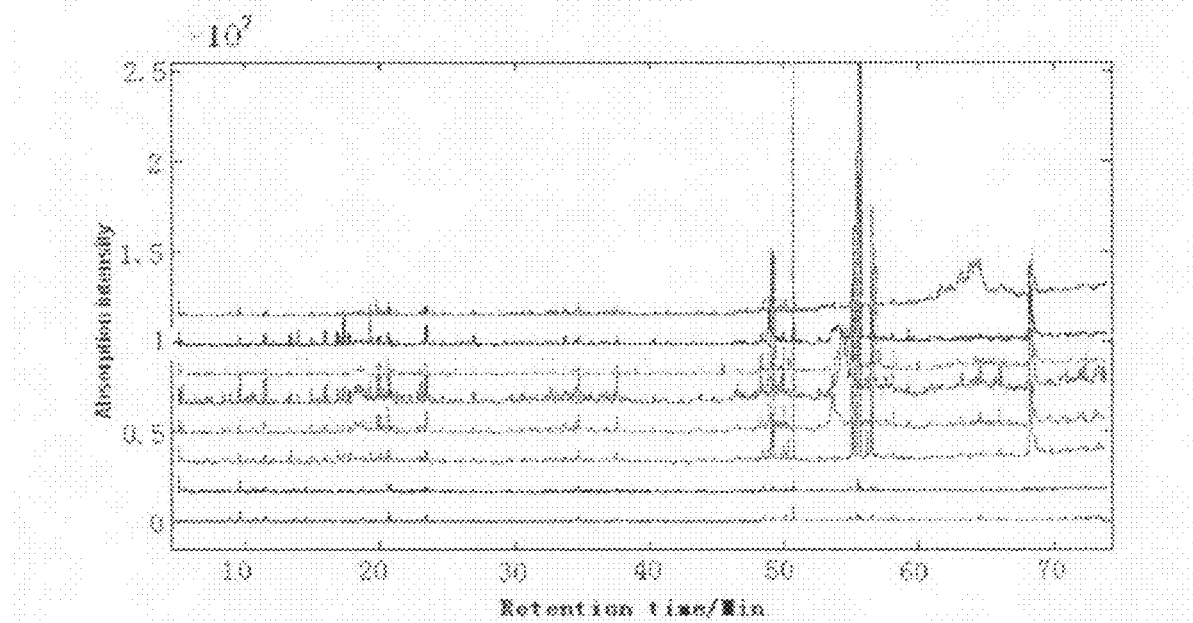
FIG. 23 illustrates a GC-MS chromatogram of ginseng extracts from lateral roots of three batches of woods-grown ginseng and five batches of mountain cultivated ginseng after calibration.
Figure 24:
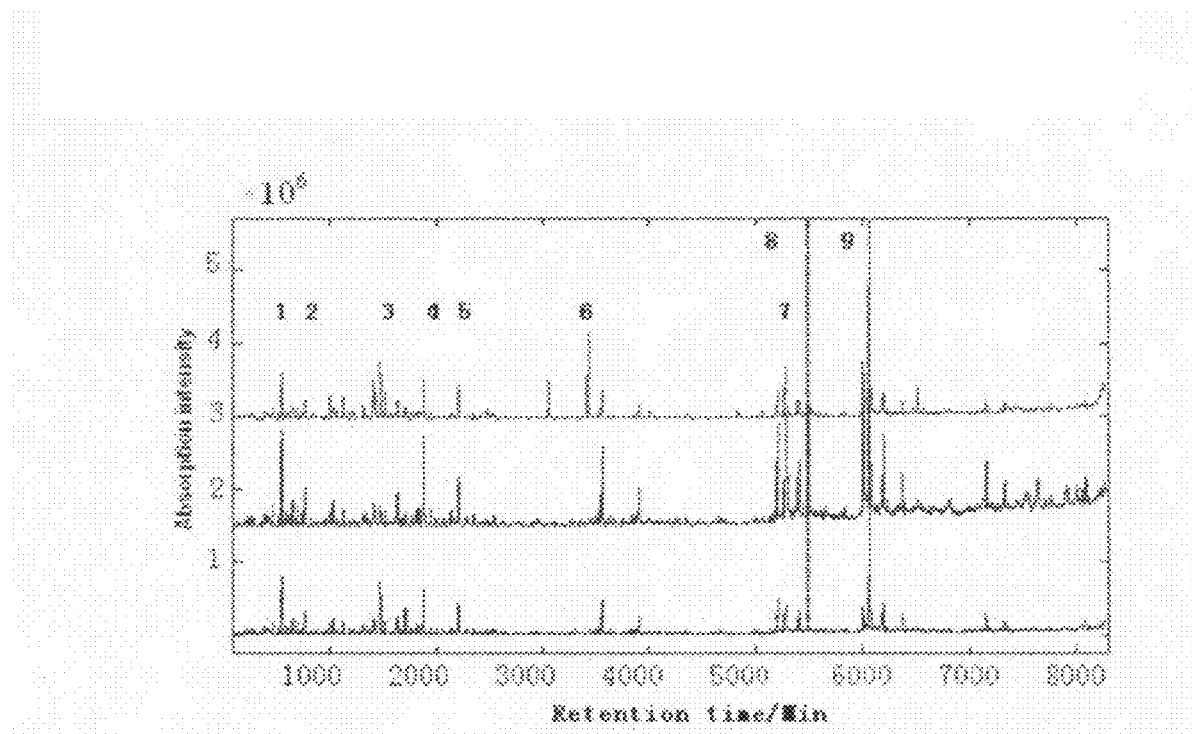
FIG. 24 illustrates a GC-MS chromatogram of ginseng extracts from rootlets of three batches of woods-grown ginseng after calibration.
Figure 25:
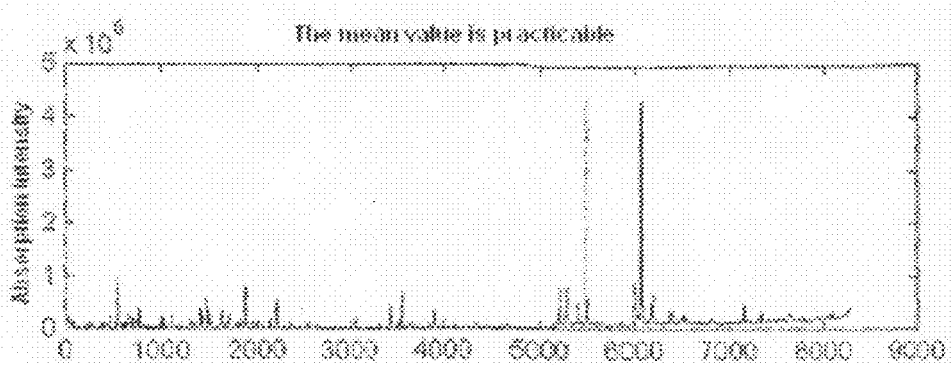
FIG. 25 illustrates a GC-MS chromatogram of a standard of ginseng extracts from rootlets of three batches of woods-grown ginseng (mean value)
Figure 26:
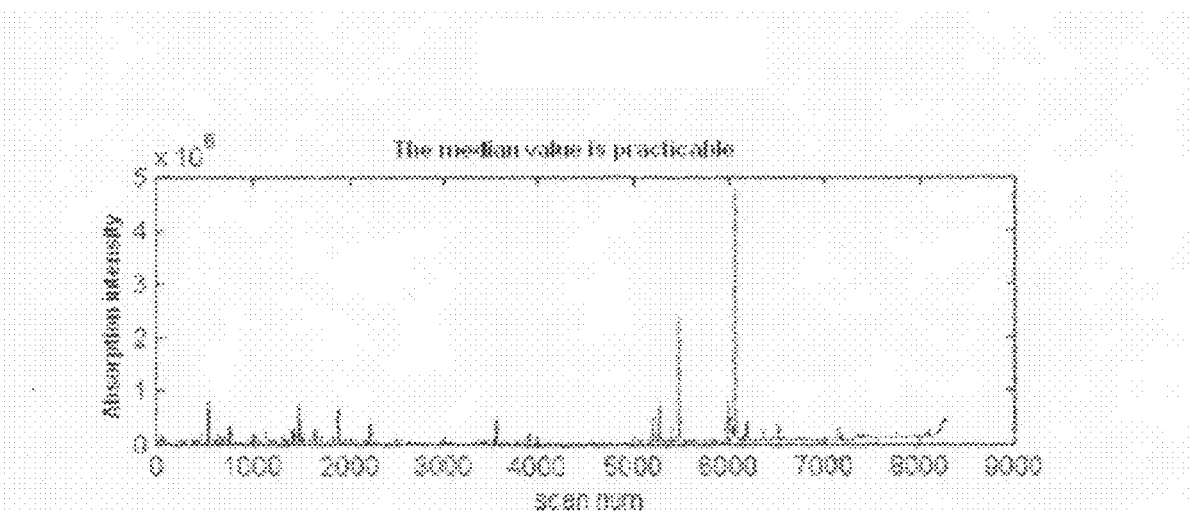
FIG. 26 illustrates a GC-MS chromatogram of a standard of ginseng extracts from rootlets of three batches of woods-grown ginseng (median value)
Figure 27:
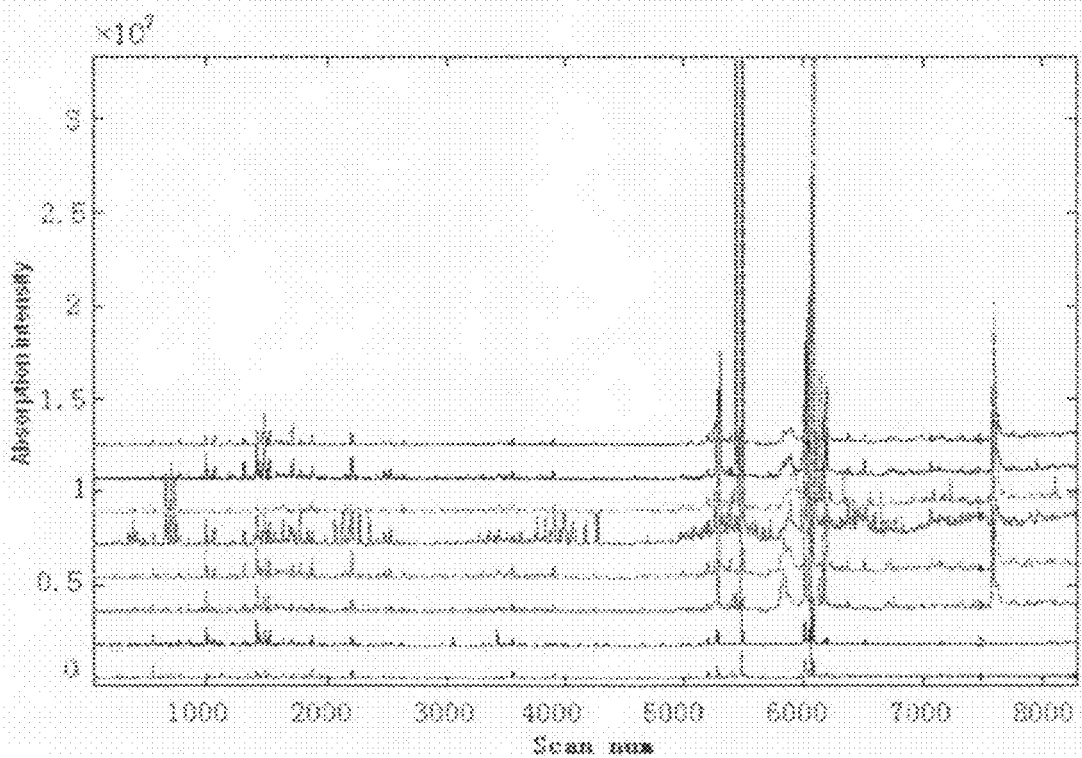
FIG. 27 illustrates a GC-MS chromatogram of ginseng extracts from rootlets of three batches of woods-grown ginseng and five batches of mountain-cultivated ginseng after calibration.

With the woods-grown ginseng established by the above method as standard, the similarity of the GC-MS chromatograms of woods-grown ginseng and mountain cultivated ginseng was calculated (FIG. 16). The result is as follows (Table 10):

TABLE 10

Similarity between Different Samples of Mountain cultivated Ginseng and Standard of Rootlets of Woods-grown Ginseng

| Chromatogram No. | Sample No. | Sample | Related Coefficient (median value) | Related Coefficient (mean value) |
|---|---|---|---|---|
| 2 | 5 | woods-grown ginseng (15-year-old) | 0.9514 | 0.9168 |
| 3 | 6 | woods-grown ginseng (18-year-old) | 0.8126 | 0.9134 |
| 3 | 7 | mountain cultivated ginseng (6-year-old) | 0.6187 | 0.7100 |
| 4 | 8 | mountain cultivated ginseng (5-year-old) | 0.6116 | 0.7056 |
| 5 | 9 | mountain cultivated ginseng (4-year-old) | 0.6121 | 0.6604 |
| 6 | 10 | mountain cultivated ginseng (5-year-old) | 0.2525 | 0.2339 |
| 7 | 11 | mountain cultivated ginseng (6-year-old) | 0.6009 | 0.6465 |

4. Conclusion

The samples of woods-grown ginseng and mountain cultivated ginseng can be well distinguished from each other by similarity calculation of GC-MS fingerprint of the main root, lateral root and rootlets. (Table 11 and Table 12)

TABLE 11

Similarity (median value) between Different Samples of Mountain cultivated Ginseng and Standard of Woods-grown Ginseng

| Sample | Related coefficient (median value) | | |
|---|---|---|---|
|  | Main root | Lateral root | Rootlets |
| Woods-grown ginseng | 0.88-0.91 | 0.78-0.96 | 0.81-0.96 |
| Mountain cultivated ginseng | 0.38-0.57 | 0.24-0.57 | 0.25-0.61 |

TABLE 12

Similarity (median value) between Different Samples of Mountain cultivated Ginseng and Standard of Woods-grown Ginseng

| Sample | Related coefficient (mean value) | | |
|---|---|---|---|
|  | Lateral root | Lateral root | Rootlets |
| Woods-grown ginseng | 0.77-0.88 | 0.78-0.96 | 0.90-0.92 |
| Mountain cultivated ginseng | 0.36-0.54 | 0.24-0.58 | 0.24-0.71 |

Woods-grown ginseng and mountain cultivated ginseng can be distinguished from each other using the similarity coefficient calculation using standards based on GC-MS fingerprint of the main root, lateral root and rootlets.

Example 2

Identification of ginseng powder sample: sample: 2 samples of ginseng powder, marked as A and B respectively, were analyzed by gas chromatogram described as described above. Similarity calculation was conducted to the obtained GC-MS chromatograms. Because the main root in the ginseng sample generally accounts for 70-90% of the total weight of ginseng, the GC-MS chromatograms of the unknown sample and the GC-MS standard of main root in woods-grown ginseng were compared, and the result is as follows (normally, if identity of the part of ginseng from which extracts were made is known, extracts from main roots are compared to the main root standard, extracts from lateral roots are compared to the lateral root standard, and extracts from rootlets are compared to the rootlet standard):

TABLE 13

Similarity Calculation and Identification Results between Unknown Ginseng Samples and Standard of Woods-grown Ginseng (Main Root)

| Sample No | Related coefficient (median value) | Related coefficient (mean value) | Identification Result |
|---|---|---|---|
| A | 0.7051 | 0.7380 | woods-grown ginseng |
| B | 0.3871 | 0.3568 | Mountain cultivated ginseng |

Result is as follows: A was woods-grown Ginseng, B was Mountain cultivated ginseng.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

What is claimed is:

1. A method for distinguishing between woods-grown ginseng and mountain-cultivated ginseng, comprising:
   (a) preparing a ginseng extract of a woods-grown ginseng or mountain-cultivated ginseng sample;
   (b) obtaining a GC-MS spectrum of said extract;
   (c) calculating a similarity coefficient based on at least 8 peaks in the GC-MS spectrum with respect to a selected standard; said selected standard being a set of at least 8 peaks in GC-MS spectrum of known woods-grown ginseng; and
   (d) comparing the similarity coefficient calculated in step (c) to pre-determined standard similarity coefficients of (i) known mountain-cultivated ginseng with respect to known woods-grown ginseng and (ii) known woods-grown ginseng with respect to known woods-grown ginseng, based on at least 8 peaks in GC-MS spectrum.

2. The method of claim 1, wherein said standard similarity coefficients are:
   for woods-grown ginseng:
      main root 0.88-0.91 median mode, 0.77-0.88 mean value mode;
      lateral root 0.78-0.96 median mode, 0.78-0.96 mean value mode;
      fibrous root 0.81-0.96 median mode, 0.90-0.92 mean value mode;
   for mountain cultivated ginseng:
      main root 0.38-0.57 median mode, 0.36-0.54 mean value mode;
      lateral root 0.24-0.57 median mode, 0.24-0.58 mean value mode;
      fibrous root 0.25-0.61 median mode, 0.24-0.71 mean value mode.

3. The method of claim 1, wherein, said GC-MS spectrum is obtained at a column temperature rising from 100° C. to 170° C. at 1.5° C./min, then from 170° C. to 190° C. at 8.0° C./min and at last from 190° C. to 240° C. at 2.0° C./min.

4. The method of claim 1, wherein said peaks are common to woods-grown ginseng and mountain-cultivated ginseng samples.

5. A method for distinguishing between woods-grown ginseng and mountain-cultivated ginseng, comprising:
   (a) preparing a ginseng extract of a woods-grown ginseng or mountain-cultivated ginseng sample;
   (b) obtaining a GC-MS spectrum of said extract;
   (c) calculating a similarity coefficient based on at least a first set of 8 peaks in the GC-MS spectrum with respect to a selected standard; said selected standard being a second set of at least 8 peaks in GC-MS spectrum of known woods-grown ginseng, said second set of at least 8 peaks being selected from peaks corresponding to: 5-methyltetradecane, 5-isobutylnonane, 5-butylnonane, β-panasinsene, p-acetylacetophenone, paeonal, [1aR-(1aα,7α,7aα,7bα)]-1a,2,3,5,6,7,7a,7b-Octahydro-(1,1,7,7a-tetramethyl-1H-cyclopropa[a]naphthalene, α-caryophyllene, [1aR-(1aα.,4aα,7α,7aβ,7bα)]-Decahydro-1,1,7-trimethyl-4-methylene-1H-cycloprop[e]azulene, isocaryphyilene, 8-methylheptadecane, n-elcosane, crocetane, falcarinol, cis,cis-linoleic acid; and
   (d) comparing the similarity coefficient calculated in step (c) to pre-determined standard similarity coefficients of (i) known mountain-cultivated ginseng with respect to known woods-grown ginseng and (ii) known woods-grown ginseng with respect to known woods-grown ginseng, based on at least 8 peaks in GC-MS spectrum.

6. The method of claim 5, wherein said standard similarity coefficients are:
   for woods-grown ginseng:
      main root 0.88-0.91 median mode, 0.77-0.88 mean value mode;
      lateral root 0.78-0.96 median mode, 0.78-0.96 mean value mode;
      fibrous root 0.81-0.96 median mode, 0.90-0.92 mean value mode;
   for mountain cultivated ginseng:
      main root 0.38-0.57 median mode, 0.36-0.54 mean value mode
      lateral root 0.24-0.57 median mode, 0.24-0.58 mean value mode
      fibrous root 0.25-0.61 median mode, 0.24-0.71 mean value mode.

7. The method of claim 5, wherein, said GC-MS spectrum is obtained at a column temperature rising from 100° C. to 170° C. at 1.5° C./min, then from 170° C. to 190° C. at 8.0° C./min and at last from 190° C. to 240° C. at 2.0° C./min.

8. The method of claim 5, wherein said peaks are common to woods-grown ginseng and mountain-cultivated ginseng samples.

9. A method for distinguishing between woods-grown ginseng and mountain-cultivated ginseng, comprising:
   (a) preparing a ginseng extract of a woods-grown ginseng or mountain-cultivated ginseng sample, said sample being of a plant part selected from a main root, a lateral root, or a rootlet;
   (b) obtaining a GC-MS spectrum of said extract;
   (c) calculating a similarity coefficient based on at least a first set of 8 peaks in the GC-MS spectrum with respect to a selected standard; said selected standard being a second set of at least 8 peaks in GC-MS spectrum of known woods-grown ginseng of the same plant part as in step (a), said second set of at least 8 peaks being selected from peaks coffesponding to: 5-methyltetradecane, 5-isobutylnonane, 5-butylnonane, β-panasinsene, p-acetylacetophenone, paeonal, [1aR-(1aα,7α,7aα,7bα)]-1a,2,3,5,6,7,7a,7b-Octahydro-1,1,7,7a-tetramethyl-1H-cyclopropa[a]naphthalene, α-caryophyllene, [1aR-(1aα.,4aα,7α,7aβ,7bα)]-Decahydro-1,1,7-trimethyl-4-methylene-1H-cycloprop[e]azulene, isocaryphyilene, 8-methylheptadecane, n-elcosane, crocetane, falcarinol, cis,cis-linoleic acid; and
   (d) comparing the similarity coefficient calculated in step (c) to pre-determined standard similarity coefficients of (i) known mountain-cultivated ginseng with respect to known woods-grown ginseng, each of the same plant part as in step (a), and (ii) known woods-grown ginseng with respect to known woods-grown ginseng, each of the same plant as in step (a), based on at least 8 peaks in GC-MS spectrum.

10. The method of claim 9, wherein said standard similarity coefficients are:
    for woods-grown ginseng:
       main root 0.88-0.91 median mode, 0.77-0.88 mean value mode
       lateral root 0.78-0.96 median mode, 0.78-0.96 mean value mode
       fibrous root 0.81-0.96 median mode, 0.90-0.92 mean value mode for mountain cultivated ginseng:
- main root 0.38-0.57 median mode, 0.36-0.54 mean value mode
- lateral root 0.24-0.57 median mode, 0.24-0.58 mean value mode
- fibrous root 0.25-0.61 median mode, 0.24-0.71 mean value mode.

11. The method of claim 9, wherein, said GC-MS spectrum is obtained at a column temperature rising from 100° C. to 170° C. at 1.5° C./min, then from 170° C. to 190° C. at 8.0° C./min and at last from 190° C. to 240° C. at 2.0° C./min.

12. The method of claim 9, wherein said peaks are common to woods-grown ginseng and mountain-cultivated ginseng samples.

* * * * *